United States Patent [19]

Baiel et al.

[11] 4,161,429

[45] Jul. 17, 1979

[54] HIGH-PRESSURE AZEOTROPIC DISTILLATION FOR THE MANUFACTURE OF ANHYDROUS ALCOHOLS

[75] Inventors: James J. Baiel, Morris Plains; Constantine Tsonopoulos, Parsippany, both of N.J.

[73] Assignee: Exxon Research & Engineering Co., Florham Park, N.J.

[21] Appl. No.: 734,953

[22] Filed: Oct. 22, 1976

[51] Int. Cl.$^2$ .................. B01D 3/36; C07C 29/28; C07C 31/08; C07C 31/10
[52] U.S. Cl. .................................. 203/18; 203/19; 203/26; 203/68; 203/70; 203/91; 568/913
[58] Field of Search .................... 203/18, 19, 68, 70, 203/63, 91, 21, 26, 4; 260/643 R; 568/913

[56] References Cited

U.S. PATENT DOCUMENTS

| | | | |
|---|---|---|---|
| 1,676,700 | 7/1928 | Lewis | 203/19 |
| 1,676,735 | 7/1928 | Keyes | 203/19 |
| 1,911,829 | 5/1933 | Lebo | 203/18 |
| 2,000,043 | 5/1935 | Shiffler et al. | 203/18 |
| 2,358,193 | 9/1944 | Wentworth | 203/19 |
| 2,619,452 | 11/1952 | Jones et al. | 203/4 |
| 2,640,017 | 5/1953 | Graff | 203/18 |
| 2,787,586 | 4/1957 | Catterall | 203/18 |
| 3,100,741 | 8/1963 | Rogillio | 203/18 |
| 3,156,630 | 11/1964 | Fahnoe et al. | 203/4 |
| 3,256,355 | 6/1966 | Gelman et al. | 203/21 |
| 3,265,590 | 8/1966 | Redcay | 203/21 |
| 3,496,240 | 2/1970 | Sturzenegger | 203/4 |
| 3,575,818 | 4/1971 | West | 260/643 R |

OTHER PUBLICATIONS

Technique of Organic Chemistry, vol. IV, *Distillation –* Weissberger, 1965 (pp. 761-763).

*Primary Examiner*—Wilbur L. Bascomb, Jr.
*Attorney, Agent, or Firm*—C. L. Kim

[57] ABSTRACT

A unique combination of specially chosen entrainers, e.g., pentanes and cyclohexane, and high-pressure azeotropic distillation conditions, e.g., 100-200 psig., provides an economically efficient separation of a $C_2$-$C_5$ alkyl alcohol, e.g., isopropanol, from its aqueous mixture; and also results in the production of a useable steam having a sufficient pressure, e.g., from 10 psig. to 30 psig. Preferably, said azeotropic distillation is conducted in the substantial absence of oxygen, e.g., less than 1 wppm.

7 Claims, 1 Drawing Figure

AZEOTROPIC DISTILLATION PROCESS FOR THE MANUFACTURE
OF HIGH-QUALITY LOWER ALKANOLS

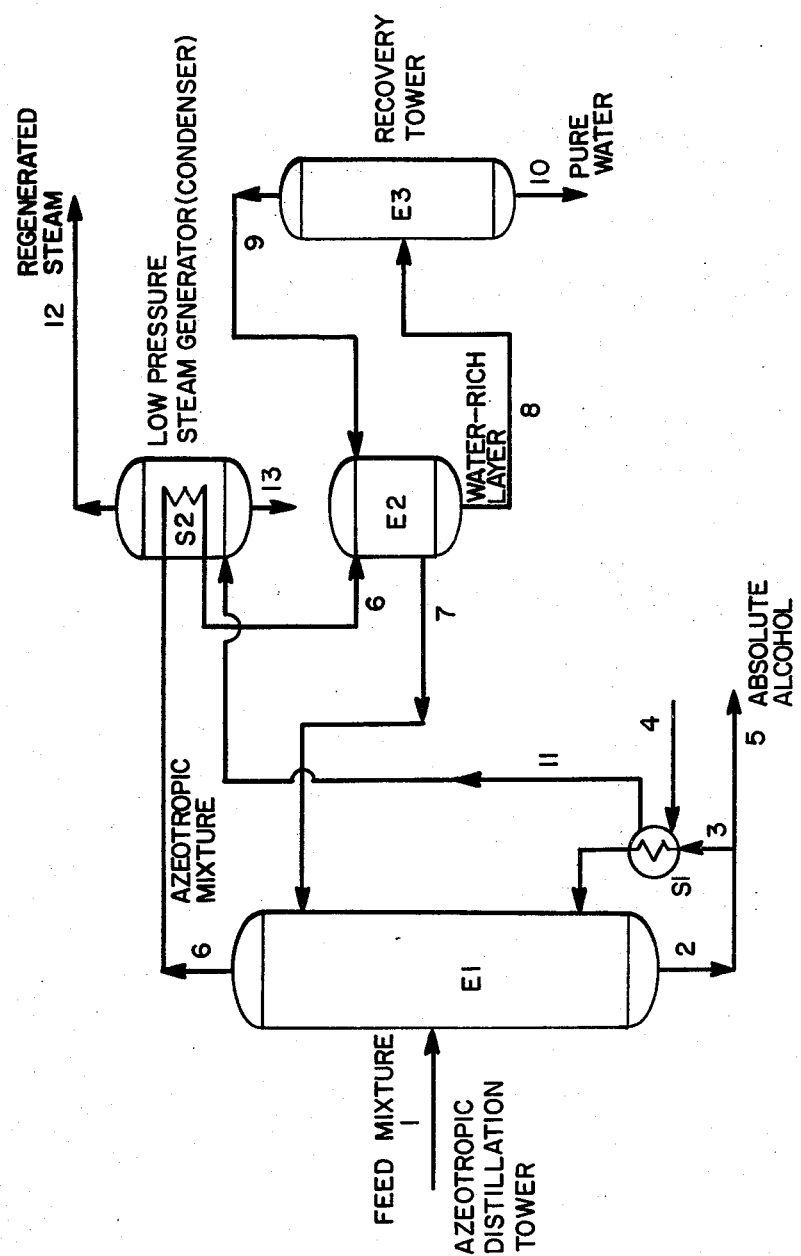

HIGH-PRESSURE AZEOTROPIC DISTILLATION FOR THE MANUFACTURE OF ANHYDROUS ALCOHOLS

BACKGROUND OF THE INVENTION

1. Field of the Invention

The present invention relates to an improved high-pressure separation process for the manufacture of anhydrous lower alkyl alcohols by employing specifically chosen entrainers. More specifically, it pertains to a high-pressure azeotropic distillation process for producing a high-quality product of a $C_2$ to $C_5$ alkyl alcohol, e.g., isopropanol, and also regenerating a useable steam of sufficient pressures, e.g., 10 to 30 psig. by employing a high pressure steam of, e.g., 125 to 225 psig., and specially chosen entrainers, e.g., pentanes and cyclohexane.

2. Description of the Prior Art

Various cyclic and acyclic hydrocarbons such as cyclohexane, methylcyclohexane, cyclopentane, methyl cyclopentane, benzene, pentanes, hexanes, isopropyl ether, ethyl ether and the like have been suggested as entraining agents for the purification of lower alkanols via azeotropic distillation. For example, U.S. Pat. No. 3,239,435 (Conseiller et al.; 1966) discloses that mixtures of aqueous alcohols can be separated under atmospheric pressure by employing cyclohexane as the entrainer. Benzene has also been widely utilized particularly in low-pressure, e.g., 0–40 psig., separation systems of lower alkanols.

With the soaring energy cost and expanding awareness of potential deleterious effects of various chemicals in human bodies and environments, today's chemical industry, including the manufacturing industry of lower alcohols, is faced with tremendous ecological, toxicological and economical challenges. Conventional methods of producing anhydrous alcohols such as the ones discussed above, however, are inadequately designed to meet the socioeconomic challenges. The common low-pressure azeotropic distillation operations are less economic due to their large consumption of energy; and, furthermore, the use of benzene has recently aroused greater concern due to its potential safety and carcinogenic hazards. Accordingly, the need has existed for an effective commercial process for manufacturing high-quality lower alcohols, which enjoy a wide variety of commercial applications such as solvents for surface coatings and printing inks, and bactericidal agents in pharmaceutical, cosmetic and toiletry products, at a lower manufacturing cost and without creating potential safety and health problems.

SUMMARY OF THE INVENTION

Applicants have now discovered that, by selecting proper entraining agents and correct combination of pressures and temperatures in the azeotropic distillation column, it is possible to regenerate a substantial amount of low-pressure steam in the overhead section of the distillation column; and also to obtain high quality, odor-free and innocuous products of essentially water-free lower alcohols. In accordance with the instant invention, an aqueous mixture of a lower alkanol, e.g., 91 volume % isopropanol binary mixture, is introduced, in the presence of a specifically chosen entrainer, e.g., cyclohexane, into a distillation column operating at a reboiler temperature in the range of from about 260° to about 375° F., preferably from about 290° to about 340° F., and more preferably from about 305° to 335° F., at an overhead temperature ranging from about 240° to 350° F., preferably from 250° to 310° F., and more preferably above about 305° F., and at a column pressure ranging from about 50 to about 300 psig., preferably from about 100 to about 200 psig., and more preferably from about 120 to about 180 psig. The reboiler of the distillation column is normally heated by an effective amount of steam having a temperature in the range of from about 300° to about 485° F., preferably from about 350° to about 390° F., and more preferably from 355° to 380° F., and a pressure in the range of from about 55 to about 600 psig., preferably from about 125 to about 225 psig., and more preferably from about 135 psig., to about 195 psig. The aqueous alcohol, when mixed with the entraining agent within the distillation column, forms a ternary azeotrope as the tops product and produces essentially water-free alcohol as the bottoms product. The tops product stream is then utilized in a condenser to regenerate as much as 0.8 to 1.0 lb. of low-pressure steam for every pound of high-pressure steam employed in the reboiler. The tops product is then sent to a decanter; and allowed to form two liquid phase layers: organic-rich phase and water-rich phase. The organic rich phase which contains major portions of the entrainer and the alcohol is then recycled to the distillation tower; while the water-rich phase is routed to a recovery tower where the entrainer and the alcohol are further removed from water.

The aqueous lower alkanols amenable to the instant high-pressure azeotropic purification process include $C_2$–$C_5$ alkanols, and preferably $C_2$ and $C_3$ alkanols such as ethanol and particularly isopropanol. Such aqueous mixtures may contain water in the range of from about 50 to 0.01 volume %, but preferably from about 9 to 5 volume %. These aqueous mixtures are available from the production streams of the alcohols manufactured from olefins, e.g., isopropanol from propylene; and, thus, normally prossess a binary azeotropic composition, e.g., 91 volume % isopropanol.

The particular entrainers, which are listed below, suitable for the present invention are chosen in accordance with the following thermodynamic requirements: (1) the entrainer should be able to form a vapor-phase ternary azeotrope in the distillation column with sufficiently high boiling temperatures to regenerate in the condenser useable steam having a pressure within the range of from about 5 to about 50 psig., preferably from about 10 to 30 psig., and more preferably from about 20 to 25 psig. and a temperature ranging from about 225° to about 300° F., preferably from about 240° to about 280° F. and more preferably from about 260° to 265° F.; (2) the ternary azeotrope should be of such a composition that the upgraded alcohol to be recovered as the bottoms product be essentially free of the entrainer and water; (3) the ternary azeotrope should easily settle into separate liquid phases of different compositions, thereby facilitating the recovery of the entrainer and the alcohol from water; (4) the entrainer should be insoluble and, particularly, inert to the alcohol mixture to avoid the formation of any by-products; and, furthermore, (5) the entrainers should be innocuous and free from any safety and health hazards. Among the numerous known classes of known entrainers, only a limited number of entrainers have been found to meet the above requirements.

Entrainers, which are reasonably suitable for the high-pressure azeotropic distillation process of the instant invention, thus include: $C_5$ to $C_8$ cyclic and acyclic saturated hydrocarbons; $C_4$ to $C_6$ ethers; and also mixtures of $C_5$'s and $C_6$'s obtained from narrowboiling fraction refinery streams. Representative species are pentanes including n-pentane, hexanes, cyclohexane, methylcyclopentane, ethyl ether, isopropyl ether and the like. Benzene, which has been widely employed in the industry, is not only suspected to be carcinogenic but also incapable of generating useable steam in the overhead section of the distillation column, e.g., condenser. The benzene system must operate at low pressures, e.g., 0–40 psig., or the steam/feed ratio becomes economically excessive. Among the entrainers listed above, pentanes and, particularly cyclohexane, are preferred as they are better adapted to producing useable steam.

DESCRIPTION OF THE PREFERRED EMBODIMENTS

In a preferred embodiment cyclohexane is employed, in the substantial absence of oxygen, to produce a high-quality, water- and odor-free isopropanol having less than about 500 wppm of water and about 1 wppm of cyclohexane; and also to generate more than 0.8 lb. of useable saturated or slightly superheated steam in the overhead condenser having about 20 to 25 psig. per every pound of high pressure, e.g., 125 to 225 psig., steam employed in the reboiler of the distillation column. As one would normally expect, however, various operating difficulties may arise in a distillation column which employs high temperatures and pressures as the hydrocarbons tend to be more reactive under such conditions. Such undesirable side reactions often produce various odor-causing impurities, thereby rendering the entire processing schemes less useful.

Applicants have, after repeated investigations and research efforts, discovered that malodorous byproduct substance, which is normally detected in the high-pressure azeotropic separation system employing cyclohexane, can be eliminated by reducing the level of oxygen present in the distillation column to a minimum, e.g., 1 wppm. In order to obviate the oxygen contamination of the alcohol purification system, therefore, it is preferred to purge the distillation tower with a nitrogen stream when possible; and more importantly, to avoid the exposure of the alcohol feedstock to oxygen, e.g., by storing the feedstock under a nitrogen pressure.

This preferred and other embodiments may be better understood by reference to the attached drawing which illustrates a simplified, steady-state version of the azeotropic distillation process for the separation of lower alkanols. The alcohol feedstock, which normally has the composition of an alcohol/water binary azeotrope, e.g., 91 vol. % isopropanol/9 vol. % water, is fed into the azeotropic distillation column (E1). In a steady-state operation system, the addition of a fresh stream of entrainer is not necessary since the entraining agent is continuously recovered and recycled through line 7 back to tower E1. Thermal energy needed to form the alcohol/entrainer/water azeotrope, which is removed from E1 through line 6, is provided through heat exchanger S1 wherein a portion of the bottoms alcohol product, transferred through line 3, is heated by an effective amount of high-pressure steam supplied through line 4. This high-pressure steam is then converted to high-temperature water which may be optimally used in preheating the feedstock (not shown), and, thereafter, sent to condenser S2 via line 11.

The tops product taken from tower E1 through line 6 is then passed through condenser S2 to generate useful low-pressure steam by vaporizing the high-temperature water supplied by way of line 11. The regenerated steam is then sent through line 12 to other facilities for utilization. A portion of the high-temperature water is sent to a condensate recovery tank through line 13.

The tops product stream, leaving S2, is then routed to decanter E2 wherein an organic-rich layer and a water-rich layer are formed. The organic-rich layer contains major portions of the alcohol and the entrainer which constituted the ternary azeotrope taken from the azeotropic distillation tower (E1). Accordingly, it is recycled through line 7 to tower E1 as the primary source of the entrainer.

The water-rich layer, on the other hand, is routed through line 8 to a recovery tower (E3) in order to further collect the entrainer and alcohol residues. The recovery tower, which is normally a lower-pressure fractional distillation column, produces essentially pure water as its bottoms product (taken through line 10) and an enriched composition of alcohol and entrainer as its tops product (line 9). This stream of alcohol and entrainer fractionated in tower E3 is then sent via line 9 back to decanter E2.

The following examples further illustrate the present invention.

EXAMPLE 1

This example documents the actual operating conditions and data, which have been scaled to a reference feedrate of 100 lb/hr isopropanol, obtained from a plant test of an azeotropic separation system similar to the one depicted in the drawing. It can be readily recognized from the data summarized in Table I that more than 0.87 pound of 22 psig. steam can be regenerated in condenser S2 for every pound of 175 psig. steam consumed in heat exchanger S1. This high rate of steam regeneration is highly significant especially in view of the fact that today's price differential between equal amounts of 175 psig. saturated steam and 22 psig. saturated steam is less than 10 percent of the price for the 22 psig. steam.

TABLE I.

Plant Test Data[1] for the Azeotropic Distillation of Isopropanol with Cyclohexane Entrainer[2]

| Stream No.[3] (Flow Rate, lb/hr) | 1 | 4 | 5 | 6 | 7 | 8 | 9 | 10 | 11 | 12 | 13 |
|---|---|---|---|---|---|---|---|---|---|---|---|
| Isopropanol | 100 | | 100 | 278 | 278 | 2.7 | 2.7 | | | | |
| Cyclohexane | | | | 408 | 408 | | | | | | |
| Water | 13.8 | | 0.01 | 67.8 | 54 | 15.6 | 1.8 | 13.8 | 215 | | 27[5] |
| Steam | | 215[4] | | | | | | | | 188[6] | |

Notes:
[1] Data adjusted to 100 lb/hr of isopropanol feed rate.
[2] Azeotropic Distillation Column (E1) Conditions:

TABLE I.-continued
Plant Test Data[1] for the Azeotropic Distillation of Isopropanol with Cyclohexane Entrainer[2]

| Stream No.[3] (Flow Rate, lb/hr) | 1 | 4 | 5 | 6 | 7 | 8 | 9 | 10 | 11 | 12 | 13 |
|---|---|---|---|---|---|---|---|---|---|---|---|

| | Pressure | Temperature |
|---|---|---|
| Reboiler | 135 psig. | 318° F. |
| Overhead | 135 psig. | 286° F. |

[3]Stream numbers correspond to the line numbers specified in the drawing
[4]Steam pressure = 175 psig.
[5]Water temperature = 263° F.
[6]Steam pressure = 22 psig.

EXAMPLE 2

A series of plant tests was run in order to determine the functional relationship between the level of oxygen within the azeotropic distillation, which oxygen is normally introduced via the aqueous alcohol feedstream, and the formation of ordor-causing impurities. The data listed in Table II indicate that the oxygen content in the feedstream should be at least lower than 6.6 wppm based on the feedmixture.

TABLE II
Effect of Oxygen in Isopropanol[1]
Purification Using Cyclohexane Entrainer

| Test No. | $O_2$ Level in 91 Vol. % Isopropanol Feed | Result |
|---|---|---|
| 1 | 1 wppm | No Odor |
| 2 | 7 wppm | "Green/Sour" Odor |
| 3 | 7.2 wppm | "Green/Sour" Odor |
| 4 | 6.6 wppm | "Green/Sour" Odor |
| 5 | 0.4 wppm | No Odor |

Note:
[1]Feed consists of 91 vol. % isopropanol and 9 vol. % water.

What is claimed is:

1. A process for the manufacture of a substantially anhydrous $C_2$-$C_5$ alcohol from an aqueous mixture thereof by employing a distillation column with the simultaneous generation of a useable steam at the overhead section of the distillation column which comprises conducting the separation of said alcohol from said aqueous mixture in the distillation column at a column pressure ranging from about 50 psig. to about 300 psig. in the presence of cyclohexane and in the presence of oxygen in an amount less than about 6.6 wppm within the distillation column.

2. The process of claim 1 wherein said useable steam generated at the overhead section of the distillation column has a pressure ranging from about 5 psig. to about 50 psig.

3. The process of claim 1 wherein said column pressure ranges from about 100 psig. to about 200 psig. and the pressure of said generated steam ranges from about 10 psig. to about 30 psig.

4. The process of claim 1 wherein the pressure of said generated steam ranges from about 20 psig. to about 25 psig.

5. The process of claim 1 wherein said aqueous alcohol mixture contains a $C_2$ to $C_3$ alkyl alcohol.

6. The process of claim 5 wherein said alcohol is ethanol.

7. The process of claim 5 wherein said alcohol is isopropanol.

* * * * *